United States Patent [19]
Russo

[11] Patent Number: 5,718,691
[45] Date of Patent: Feb. 17, 1998

[54] GASTROSTOMY FEEDING PORT WITH A POSITIVELY SEALING ONE-WAY ENTRANCE VALVE

[76] Inventor: Ronald D. Russo, 8 Candleberry Rd., Barrington, R.I. 02806

[21] Appl. No.: 202,443

[22] Filed: Feb. 28, 1994

[51] Int. Cl.$^6$ ............................................... A61M 5/00
[52] U.S. Cl. ........................ 604/247; 604/256; 604/335
[58] Field of Search ................................. 604/247, 256, 604/268, 335, 337

[56] References Cited

U.S. PATENT DOCUMENTS

| | | |
|---|---|---|
| 3,853,127 | 12/1974 | Spademan . |
| 3,977,400 | 8/1976 | Moorehead . |
| 4,351,328 | 9/1982 | Bodai . |
| 4,430,081 | 2/1984 | Timmermans . |
| 4,673,393 | 6/1987 | Suzuki et al. ............................ 604/167 |
| 4,850,953 | 7/1989 | Haber et al. . |
| 4,944,732 | 7/1990 | Russo . |
| 5,000,745 | 3/1991 | Guest et al. . |
| 5,073,166 | 12/1991 | Parks et al. . |
| 5,114,408 | 5/1992 | Fleischhaker et al. . |
| 5,125,897 | 6/1992 | Quinn et al. . |
| 5,125,903 | 6/1992 | McLaughlin et al. . |
| 5,167,637 | 12/1992 | Okada et al. ............................ 604/167 |
| 5,261,885 | 11/1993 | Lui . |
| 5,279,571 | 1/1994 | Larkin ............................ 604/167 |
| 5,336,203 | 8/1994 | Goldhardt et al. ............................ 604/247 |

*Primary Examiner*—Michael Powell Buiz
*Assistant Examiner*—N. Kent Gring
*Attorney, Agent, or Firm*—Woodard, Emhardt, Naughton, Moriarty & McNett

[57] ABSTRACT

A gastrostomy feeding port is disclosed which incorporates a seal module which includes a valve housing and a resilient valve member contained therein. The valve housing defines an inner passageway to provide fluid communication into a long term indwelling catheter and includes a rigid compression collar portion which defines a valve member receiving cavity within the inner passageway. The resilient valve member has a diaphragm portion which has an "S" shaped slit therethrough, and an outer peripheral edge which generally conforms in shape to the valve member receiving cavity but is larger in dimension than the cavity when uncompressed. The resilient valve member also includes an outer wall portion which extends away from the outer peripheral edge of the diaphragm portion and which generally conforms in shape to the cavity. The resilient valve member is compressively fitted within the receiving cavity by the advancing of the outer wall portion into said cavity to thereby cause the outer peripheral edge to be compressed in dimension to fit within the cavity, with the compression collar pressing inwardly against the outer peripheral edge of the diaphragm portion to apply laterally compressive forces which bias the slit toward a normally closed position.

11 Claims, 3 Drawing Sheets

GASTROSTOMY FEEDING PORT WITH A POSITIVELY SEALING ONE-WAY ENTRANCE VALVE

BACKGROUND OF THE INVENTION

This invention relates to medical devices, and particularly relates to gastrostomy feeding ports which use check valves to prevent reflux of gastric contents out the entrance opening of the device during use.

Gastrostomy feeding ports provide access to the stomach at a stoma site. Such ports are typically left in place over a prolonged period of time and are used for feeding and medicating the patient over this period. Some of these devices include check valves which serve to prevent the reflux of gastric contents through the port because the leakage of gastric contents, which is highly acidic, can cause severe skin burns or tissue maceration leading to chronic skin infections. Valves that have been used in prior art gastrostomy feeding ports, however, do not always work as intended to prevent reflux, particularly after many repeated uses. Consequently, gastrostomy feeding ports are often supplied with closure caps which positively seal the port entrance while the port is not being used.

Gastrostomy feeding ports are usually short in length, low profile, and fit fairly flush to the skin surface. U.S. Pat. No. 4,944,732 describes one such device, which is commercially available as the Gastro-Port from Sandoz Nutrition Corp. The Gastro-Port includes an anti-reflux valve which is located outside the body in a removable screw cap. Since the valve portion is removable it can be repaired or replaced if needed without needing to replace the entire feeding port. The Button Replacement Gastrostomy Device is another commercially available gastrostomy feeding port which includes an anti-reflux valve. In the Button device, the anti-reflux valve is located in the distal tip of the device inside the stomach. Both the Button and Gastro-Port devices have closure caps to seal off or plug up the entrance opening in case the valves clog up or leak.

Other valve structures for catheter ports are shown in the prior art in the Bodai U.S. Pat. No. 4,351,328 and the hemostasis valve of Guest U.S. Pat. No. 5,000,745 and the valve of Suzuki U.S. Pat. No. 4,673,393. The Bodai valve incorporates a series of membranes which seal under the influence of the material's own resiliency. Both the Guest and Suzuki valves also provide a sealing effect owing to the resiliency of multiple stacked membrane valves with oriented slit openings to prevent leakage. These membrane structures tend to become stretched by repeated use, causing the valves to lose their ability to positively seal closed and leakage will begin to occur. Since the devices of Bodai, Guest or Suzuki are short term use devices, however, their valves structures need to function properly for only a few procedures before being removed or replaced. These valve structures are, therefore, adequate for their intended purposes, although they would not prove to be reliable over long term and repeated use.

Some devices in the general medical art have included valve structures which apply compressive force in some form against the valve opening to bias the valve towards a closed position. See, for instance, U.S. Pat. Nos. 3,853,127 to Spademan; 4,430,081 to Timmermans; 5,114,408 to Fleishhaker et al.; 5,125,903 to McLaughlin et al.; and 5,261,885 to Lui. While such devices may be satisfactory for their intended purposes, they generally do not provide a biased-diaphragm valve structure that is both easy to construct and assemble and will operate reliably through long term, repeated insertion and removal of an enteral feeding tube adapter. A long term indwelling catheter or feeding tube, on the other hand, such as a gastrostomy feeding port, needs to provide a positive seal for many repeated uses over a long period of time. Since the valves of the prior art have not provided such a reliable seal, closure caps, as discussed above, have been used to ensure that leakage does not occur. Closure caps, however, are inconvenient because they need to be removed prior to each use of the port and reapplied onto the port after each such use. Over the course of time that a single port is left in place, this would involve hundreds of times that the cap would have to be removed from and replaced back onto the port. And should the cap be forgotten or not properly closed about the port even a single time, unintended leakage may consequently occur.

Wherefore, there is a need for a new long term indwelling catheter, particularly a gastrostomy feeding port, with an entrance valve that provides a positive sealing effect over the course of many recurrent uses of the valve and over the extended period of time that the port is left in place on a patient. Such a device would eliminate the need for a closure cap and would be both safer and more convenient to use than devices that have been provided in the past.

SUMMARY OF THE INVENTION

The present invention provides a long term indwelling catheter with an improved one-way entrance seal module which will remain positively sealed closed after repeated and extensive use. The invention is especially useful when used as part of a low profile enteral gastrostomy feeding port where the valve and port might be left indwelling in a patient for up to a year and where a positive seal needs to be maintained even after hundreds of repeated uses.

A device according to the present invention incorporates a seal module which includes a valve housing and a resilient valve member contained therein. The valve housing defines an inner passageway to provide fluid communication into a long term indwelling catheter and includes a rigid compression collar portion which defines a valve member receiving cavity within the inner passageway. The resilient valve member has a diaphragm portion which has an "S" shaped slit therein and an outer peripheral edge which generally conforms in shape to the valve member receiving cavity but is larger in dimension than the cavity when uncompressed. The resilient valve member also includes an outer wall portion which extends away from the outer peripheral edge of the diaphragm portion and which generally conforms in shape to the cavity. The resilient valve member is compressively fitted within the receiving cavity by the advancing of the outer wall portion into said cavity to thereby cause the outer peripheral edge to be compressed in dimension to fit within the cavity, with the compression collar pressing inwardly against the outer peripheral edge of the diaphragm portion to apply laterally compressive forces which bias the slit toward a normally closed position.

The resilient valve member is made of a one-piece resiliently molded valve with a flat membrane. The "S" shaped slit therein is formed by two arcically shaped leaves. The valve member is cylindrically shaped and is compressively fitted into the likewise cylindrically shaped compression collar to bias the arcical leaves to a positively sealed closed position. Feeding adapters can be repeatedly inserted through the valve and connected directly with the catheter lumen to deliver unobstructed enteral formula directly into the patient. Removal of the adapter returns the valve immediately to its positively sealed position due to the compressive forces of the collar about the arcically shaped leaves.

The valve remains compressively biased towards its sealed closed position when not in use, and is not permitted to stretch or deform which can lead to leakage. The one-way entrance seal permits convenient insertion of an obturator to help in insertion of the catheter into the body and the seal also permits convenient insertion of a feeding adapter which can be used for either feeding or decompression of the stomach. It needs no separate closure plug, or removal of a screw cap, or different feeding adapters, or complicated decompression tubes. This valve structure allows the device to be lower in profile and closer to the skin surface, and helps to make the device more convenient, less complicated, and easier to use than other devices in the prior art. The device is especially useful for active children who require low profile feeding ports.

Accordingly, it is a primary object of the present invention to provide an improved one-way entrance seal module for a medical catheter.

Another object of the present invention is to provide an improved gastrostomy feeding port utilizing a one-way entrance seal.

Another object of the present invention is to provide an improved gastrostomy feeding device with an externally located entrance seal.

Another object of the present invention is to provide a gastrostomy feeding port which is less complicated, easier to use, and less expensive than other commercially available products.

Other objects, features, and advantages of the invention shall become apparent from the detailed drawings and descriptions which follow.

DESCRIPTION OF THE PREFERRED EMBODIMENT

Figure 1:
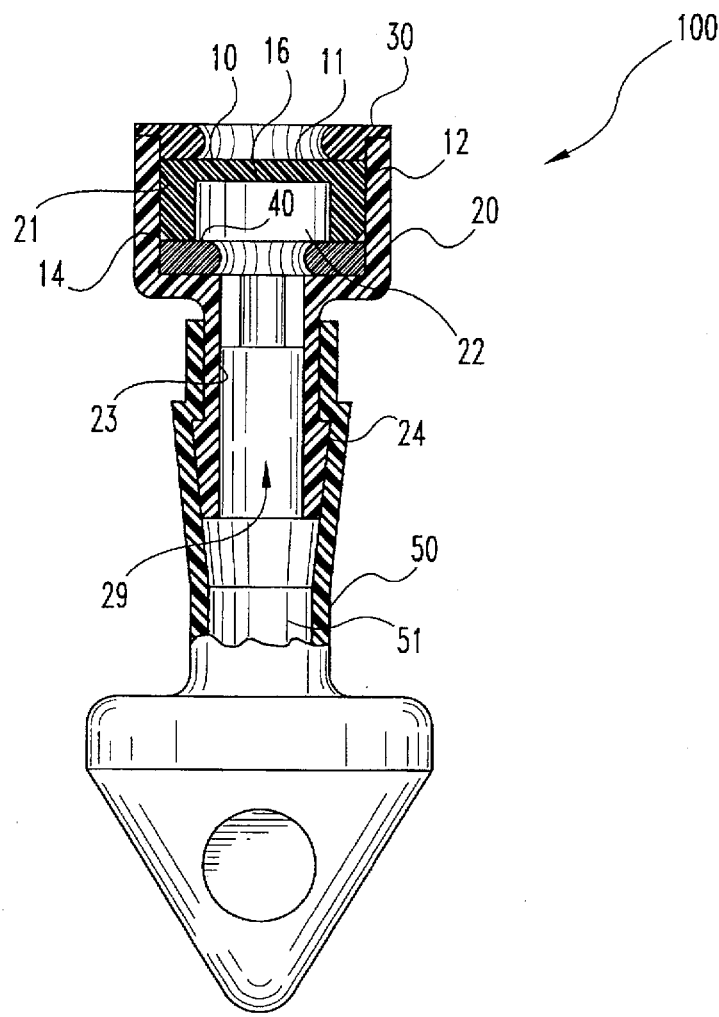
FIG. 1 is a side, partially cross-sectioned view of a gastrostomy port of the present invention incorporating a positively sealing one-way entrance valve.
Figure 2:
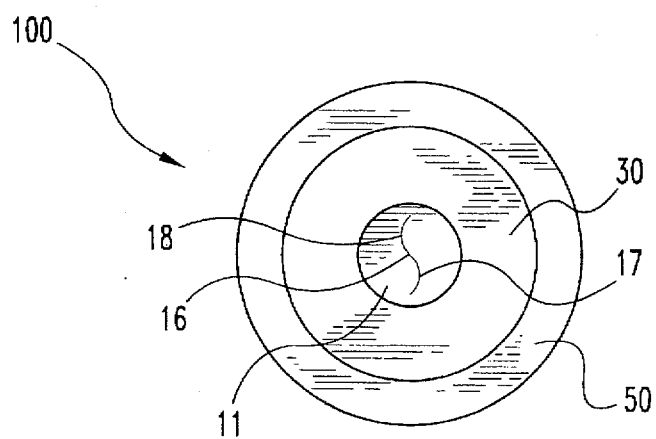
FIG. 2 is a top plan view of the gastrostomy feeding port of FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. Referring now to FIGS. 1 and 2, there is shown a gastrostomy feeding port 100 which includes resilient valve member 10, valve housing 20, retainer cap 30, O-ring seal 40, and tubular/tip member 50. Resilient valve member 10 is made of silicone rubber, and has been constructed as a molded one-piece component and is preferably made from shore A 50 to 60 durometer high tear strength medical grade silicone. Diaphragm portion 11 of valve 10 is about 0.050 inches thick and about 0.325 inches in diameter and has a centrally located S-shaped slit 16 therein. Valve member 10 further has an outer cylindrical wall portion 12 which extends downwardly from the peripheral edge of diaphragm portion 11. O-ring 40 is preferably made of medical grade silicone as well, in the range of shore A 60 to 65 hardness.

Valve housing 20 defines an inner passageway 29 therethrough and includes rigid compression collar portion 21 which defines receiving cavity 22, annular seating portion 23 for seating of an adaptor, and annular barb 24 for securing attachment to tubular/tip member 50. Valve housing 20 is injection molded from a rigid plastic such as lexan or polypropylene, but could be a machined part of stainless steel, or made of other suitable biocompatible material as well. Retainer cap 30 is preferably made of the same material as valve housing 20.

To assemble the valve structure for gastrostomy port 100, O-ring seal 40 is first placed into cavity 22 defined by compressive collar portion 21 of valve housing 20. valve member 10 is then "press" fit into valve housing 20 by first fitting outer cylindrical wall portion 12 of valve member 10 into compression collar 21 and then applying even pressure to advance valve member 10 into cavity 22. The lower portion of cylindrical wall portion 12 of valve member 10 has a chamfered edge 14 to facilitate the introduction of valve member 10 into cavity 22. Also, isopropyl alcohol, which readily evaporates, can be used as a lubricant to aid in the press fitting of valve member 10 into valve housing 20.

As valve member 10 is advanced into cavity 22, cylindrical wall portion 12 is compressed to conform to the size of cavity 22. The compression of cylindrical wall portion 12, in turn, applies an evenly distributed compressive force on diaphragm portion 11 to cause disphragm portion 11 to be evenly compressed and to thereby fit within cavity 22 without buckling or distorting. Once valve member 10 has been fully seated into valve housing 20, compression collar 21 acts with an inwardly directing compressive force to actively bias leaves 17 and 18 of "S" slit 16 on diaphragm portion 11 to positively seal valve member 10.

After valve member 10 has been seated into cavity 22, retainer cap 30 is placed on the top portion of valve housing 20 and affixed thereto. Attachment may be made by use of a suitable biocompatible solvent cement, or by ultrasonic welding. Once in place, retainer cap 30 does not exert any axial compressive force upon valve member 10, which could cause distortion of the sealing arrangement, and preferably only rests on the surface of diaphragm portion 11 or allows for a small gap therebetween.

Compression collar 21 supplies an interference fit of 0.015 inches around the entire circumference of cylindrical wall portion 12 and thus exerts an even sealing pressure on the S-slit 16 at all times. Compression collar 21 exerts this constant pressure or pre-load on leaves 17 and 18 to prevent diaphragm portion 11 from stretching or losing its resiliency when the valve is repeatedly opened or closed. Once assembled as described above, gastrostomy port 100 becomes one unitized piece with a one-way entrance valve seal accessing the central lumen of the tubular/tip member 50. The one-way valve permits only entrance into central lumen 51 and prevents any fluid from refluxing or backing up the tube and out the entrance seal.

Figure 3:
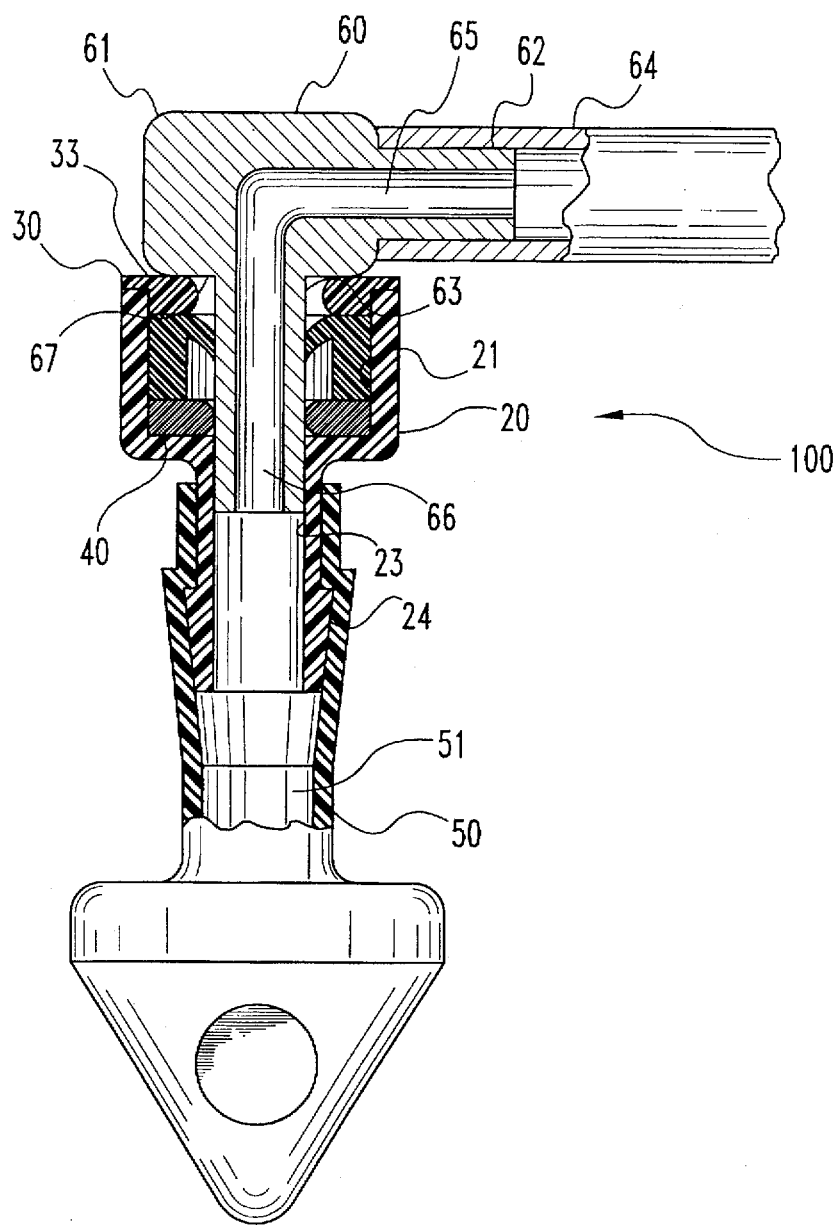
FIG. 3 is a partially cross-sectioned side view of the gastrostomy feeding port of FIGS. 1 and 2, showing a right angle adapter opening the one-way entrance seal and seated within the valve module to provide access into the catheter lumen of the feeding port.

FIG. 3 shows right angle adapter 60 opening entrance "S" slit 16 of valve member 10. Adapter 60 has a rigid injection molded right angle body portion 61, with rear stem 62 and front stem 63. Connected onto rear stem 62 is flexible PVC connecting tube 64. Rear stem 62 has lumen 65 and front stem 63 has lumen 66. When front stem 63 opens entrance seal 10, it seats into annular seating portion 23 of housing member 20. The underside surface 67 on right angle body portion 60 seats firmly on top surface 33 of retainer cap 20. So positioned, lumen 66 of front stem 63 accesses central lumen 51 of tubular/tip member 50. Right angle adapter 60 thus accesses lumen 51 of tubular/tip member 50 to deliver enteral formula or the administration of liquid medication into the body of a patient.

Adapter 60, via connecting tube 64, can be attached to any medication or enteral delivery set whether administered by gravity or a pump delivery method. In addition, adapter 60 can act as a decompression tube to vent gastrostomy port 100, and relieve pressure build up which tends to occur when a gastrostomy feeding port is left in place over a long period of time. When not in use, adapter 60 is removed and valve member 10 closes instantaneously to prevent reflux. Sealing is instantaneous due to compression collar 21 which acts to positively return leaves 17 and 18 to their normally closed position. Adapter 60 can be repeatedly inserted as needed over many months of use without the valve leaking or stretching out of shape.

As described above, a right angle adapter can be inserted into the valve S-slit 16 as needed. The valve remains in its normally closed positively sealed position due to compressive collar 21 acting to bias valve member 10 closed and keeping it closed to prevent reflux of stomach contents out through valve member 10. As such, feeding port 100 requires no internal anti-reflux valve, which might become clogged or stuck. It also does not need any removable valve cap or any stoppers or back up closure caps to add bulk to the outside profile. All functions can take place directly through the entrance seal, thus eliminating the need for anti-reflux valves, valve caps, stoppers, closure caps, or complicated decompression tubes.

Figure 4A:
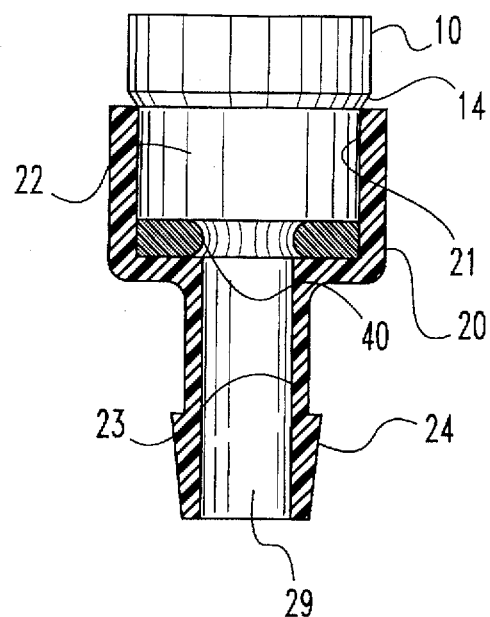
FIG. 4a is a side cross-sectioned view of the valve housing of FIGS. 1–3, showing resilient valve member 10 prior to positioning within cavity 22.
Figure 4B:
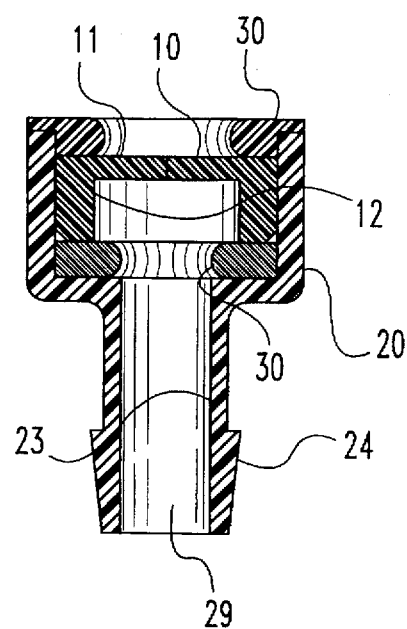
FIG. 4b is a side cross-sectioned view of valve housing 20 of FIG. 4a, showing resilient valve member press fitted into cavity 22, with retainer cap 30 mounted thereon to maintain valve member 10 within cavity 22.

FIG. 4a shows resilient valve member 10 prior to positioning within cavity 22. In FIG. 4a, valve member 10 is uncompressed and is larger in dimension than cavity 22. FIG. 4a further shows how chamfered edge 14 allows for the introduction of cylindrical wall portion 12 into cavity 22 such that valve member 10 can then be press fit into cavity 22 without buckling or distorting diaphragm portion 11. FIG. 4b, showing resilient valve member 10, after it has been press fitted into cavity 22, with retainer cap 30 mounted thereon to maintain valve member 10 within cavity 22.

As can be appreciated, variations in the form of the entrance seal can be made from that specifically described herein without departing from the spirit or scope of the underlying invention. For instance, varying configurations as to the shape of the valve and corresponding valve receiving cavity, or in the slit within the valve may still fall within the spirit and scope of this invention. With the foregoing in mind, it is apparent to anyone skilled in the art to make modifications or different configurations of the invention without varying from the invention and the invention is not limited to the particular forms herein shown and described except insofar as indicated by the scope of the appended claims.

Accordingly while the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A modular one-way entrance valve for a long term in-dwelling catheter configured for engagement by a feeding tube adapter, said valve comprising:

a valve housing, said valve housing defining an inner passageway therethrough for providing fluid communication into a long term in-dwelling catheter, said valve housing including a rigid compression collar portion which defines a valve member receiving cavity in said valve housing;

a resilient valve member, said resilient valve member including a diaphragm portion and an outer wall portion, said diaphragm portion defining a slit therethrough and having an outer peripheral edge which generally conforms in shape to said valve member receiving cavity but is larger in dimension than said cavity when said resilient valve member is uncompressed, said outer wall portion extending away from said outer peripheral edge and generally conforming in shape to said cavity; and wherein said resilient valve member is compressively fitted within said valve member receiving cavity by advancing said outer wall portion into said cavity to thereby cause said outer peripheral edge to be compressed in dimension to fit within said cavity, with said compression collar portion of said valve housing pressing inwardly against said outer peripheral edge of said diaphragm portion to apply laterally compressive forces against said diaphragm portion and to thereby bias said slit toward a normally closed position; and further wherein said valve housing includes a rigid end cap defining an orifice intersecting said valve member receiving cavity, said orifice being configured to align with said slit when said diaphragm portion is compressed within said cavity, said rigid end cap being configured to receive the feeding tube adapter stem through said orifice to pass through said slit, said end cap being spaced apart from said resilient valve member and having a top surface to provide a seat for the feeding tube adapter to prevent over-insertion of the adapter into the valve.

2. The modular one-way entrance valve for a long term indwelling catheter of claim 1 in which said valve member receiving cavity portion and said resilient valve member are generally cylindrical in shape.

3. The modular one-way entrance valve for a long term indwelling catheter of claim 1 in which the slit in said diaphragm portion is curved in shape.

4. The modular one-way entrance valve for a long term indwelling catheter of claim 1 in which the slit in said diaphragm portion is "S" in shape.

5. A gastrostomy feeding port configured for engagement by a feeding tube adapter, comprising:

catheter means for providing access into the stomach of a patient;

a valve housing engaging in said catheter means, said valve housing defining an inner passageway therethrough for providing fluid communication into said catheter means, said valve housing including a rigid compression collar portion which defines a valve member receiving cavity in said valve housing;

a resilient valve member, said resilient valve member including a diaphragm portion and an outer wall portion, said diaphragm portion defining a slit therethrough and having an outer peripheral edge which generally conforms in shape to said valve member receiving cavity but is larger in dimension than said cavity when said resilient valve member is uncompressed, said outer wall portion extending away from said outer peripheral edge and generally conforming in shape to said cavity; and wherein said resilient valve member is compressively fitted within said valve member receiving cavity by advancing said outer wall portion into said cavity to thereby cause said outer peripheral edge to be compressed in dimension to fit within said cavity, with said compression collar portion of said valve housing pressing inwardly against said outer peripheral edge of said diaphragm portion to apply laterally compressive forces against said diaphragm portion and to thereby bias said slit toward a normally closed position; and further wherein said valve housing includes a rigid end cap defining an orifice intersecting said valve member receiving cavity, said orifice being configured to align with said slit when said diaphragm portion is compressed within said cavity, said rigid end cap being configured to receive the feeding tube adapter stem through said orifice to pass through said slit, said end cap being spaced apart from said resilient valve member and having a top surface to provide a seat for the feeding tube adapter to prevent over-insertion of the adapter into the valve.

6. The gastrostomy feeding port of claim 5 in which said valve member receiving cavity portion and said resilient valve member are cylindrical in shape.

7. The gastrostomy feeding port of claim 5 in which the slit in said diaphragm portion is curved in shape.

8. The gastrostomy feeding port of claim 5 in which the slit in said diaphragm portion is "S" in shape.

9. A modular one-way entrance valve for a long term in-dwelling catheter configured for engagement by a feeding tube adapter, the valve comprising:

a valve housing defining an inner passageway therethrough for providing fluid communication into the long term in-dwelling catheter, said valve housing including:
 a rigid compression collar portion which defines a valve member receiving cavity in said valve housing,
 a connection member configured for selectively connecting the valve and long term in-dwelling catheter together,
 an end cap defining an orifice intersecting said valve member receiving cavity;

a resilient valve member, said resilient valve member including a diaphragm portion and an outer wall portion, said diaphragm portion defining a slit therethrough and having an outer peripheral edge which generally conforms in shape to said valve member receiving cavity but is larger in dimension than said cavity when said resilient valve member is uncompressed, said outer wall portion extending away from said outer peripheral edge and generally conforming in shape to said cavity; and wherein said resilient valve member is compressively fitted within said valve member receiving cavity by advancing said outer wall portion into said cavity to thereby cause said outer peripheral edge to be compressed in dimension to fit within said cavity, with said compression collar portion of said valve housing pressing inwardly against said outer peripheral edge of said diaphragm portion to apply laterally compressive forces against said diaphragm portion and to thereby bias said slit toward a normally closed position.

10. The valve according to claim 9, wherein said connection member includes a barb.

11. The valve according to claim 9, wherein said resilient valve member is positioned between said connection member and said end cap.

* * * * *